(12) United States Patent
Bäther et al.

(10) Patent No.: US 10,191,023 B2
(45) Date of Patent: Jan. 29, 2019

(54) GAS-MEASURING DEVICE (71) Applicant: Dräger Safety AG & Co. KGaA, Lübeck (DE)

(72) Inventors: Wolfgang Bäther, Lübeck (DE); Björn Raupers, Stockelsdorf (DE); Stefan Lehmann, Uetersen (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 153 days.

(21) Appl. No.: 15/110,238

(22) PCT Filed: Jan. 9, 2015

(86) PCT No.: PCT/EP2015/000028
§ 371 (c)(1),
(2) Date: Jul. 7, 2016

(87) PCT Pub. No.: WO2015/104221
PCT Pub. Date: Jul. 16, 2015

(65) Prior Publication Data
US 2016/0327532 A1    Nov. 10, 2016

(30) Foreign Application Priority Data
Jan. 11, 2014    (DE) .................. 10 2014 000 343

(51) Int. Cl.
*G01N 33/00*        (2006.01)
*G01N 27/414*       (2006.01)
(Continued)

(52) U.S. Cl.
CPC ..... *G01N 33/0029* (2013.01); *G01N 33/0009* (2013.01); *G01N 27/4141* (2013.01);
(Continued)

(58) Field of Classification Search
CPC ........... G01N 33/0009; G01N 29/2462; G01N 33/0029; G01N 27/4141; G01N 27/4077;
(Continued)

(56) References Cited
U.S. PATENT DOCUMENTS 3,906,473 A    9/1975  Le Vine
4,012,692 A    3/1977  Eicker
(Continued)

FOREIGN PATENT DOCUMENTS

CA    1017968 A     9/1977
CN    102226776 A   10/2011
(Continued)

OTHER PUBLICATIONS

Desai et al., Hypergolic fuel detection using individual single walled carbon nanotube networks, Jun. 2010, Journal of Applied Physics, pp. 1-7.*
(Continued)

*Primary Examiner* — John Fitzgerald
*Assistant Examiner* — Truong D Phan
(74) *Attorney, Agent, or Firm* — McGlew and Tuttle, P.C.

(57) ABSTRACT

A sensor unit (10) for detecting a gas is configured with a pressure-tight measuring channel (11), with a gas inlet (12) for introducing the gas into the measuring channel, with a gas outlet (13) for removing the gas from the measuring channel, and with a pump unit (14) for evacuating the measuring channel. The measuring channel has a gas sensor (15) for detecting the gas and a heating unit (16) for heating the gas sensor. The sensor unit (10) is configured to be operated in a measuring mode and in a regeneration mode. The measuring channel (11) is evacuated and the gas sensor (15) is heated in the regeneration mode.

20 Claims, 8 Drawing Sheets (51) Int. Cl.
*G01N 29/24* (2006.01)
*G01Q 60/24* (2010.01)

(52) U.S. Cl.
CPC . *G01N 29/2462* (2013.01); *G01N 2291/0215* (2013.01); *G01Q 60/24* (2013.01)

(58) Field of Classification Search
CPC .... G01N 27/12; G01N 27/407; G01N 27/414; G01N 33/005; G01N 29/024; G01N 2291/02809; G01N 2291/0256; G01N 27/122; G01Q 60/24; G08B 17/117; G08B 17/10; G08B 17/113; G08B 17/00; G08B 29/145
USPC ....... 73/31.05, 31.06, 24.01; 340/634, 693.6, 340/628
See application file for complete search history.

(56) References Cited

U.S. PATENT DOCUMENTS

| | | | |
|---|---|---|---|
| 4,185,491 A | | 1/1980 | Owen |
| 4,399,684 A | | 8/1983 | Advani et al. |
| 4,567,475 A | | 1/1986 | Bukowiecki et al. |
| 5,844,123 A | | 12/1998 | Marsh et al. |
| 6,621,848 B1 | * | 9/2003 | Ullman .................... H01S 3/036 372/34 |
| 2002/0122744 A1 | | 9/2002 | Hui et al. |
| 2003/0160956 A1 | * | 8/2003 | Chevalier ................ G01N 21/68 356/316 |
| 2004/0133348 A1 | * | 7/2004 | Kalantar-Zadeh ... G01N 29/022 702/2 |
| 2007/0189931 A1 | | 8/2007 | Ruhe et al. |
| 2007/0235773 A1 | * | 10/2007 | Eisele ................ G01N 27/4143 257/253 |
| 2008/0007267 A1 | * | 1/2008 | Prelas ..................... G01N 27/60 324/452 |
| 2008/0202211 A1 | | 8/2008 | Wetzig |
| 2009/0151429 A1 | * | 6/2009 | Jun ...................... G01N 33/0027 73/31.06 |
| 2009/0272175 A1 | * | 11/2009 | Frerichs ............. G01N 27/4143 73/25.01 |
| 2010/0000292 A1 | * | 1/2010 | Karabacak ........... G01N 29/022 73/24.01 |
| 2010/0001211 A1 | * | 1/2010 | Huang ................... B82Y 15/00 250/492.1 |
| 2011/0116079 A1 | * | 5/2011 | Tkachuk ............. G01N 21/3504 356/51 |
| 2012/0270334 A1 | * | 10/2012 | Ojeda ....................... G01N 1/40 436/178 |
| 2013/0126947 A1 | * | 5/2013 | Wilbertz ................. H01L 29/66 257/253 |
| 2013/0139570 A1 | * | 6/2013 | Senft ....................... H01L 29/66 73/31.06 |
| 2014/0208838 A1 | * | 7/2014 | Moon .................... G01N 27/16 73/114.75 |
| 2015/0056060 A1 | * | 2/2015 | Makarov ............... F04D 19/042 415/1 |

FOREIGN PATENT DOCUMENTS

| | | |
|---|---|---|
| CN | 102636564 A | 8/2012 |
| DE | 27 35 222 A1 | 2/1979 |
| DE | 19 926 747 C1 | 4/2001 |
| DE | 10 2005 050 914 A1 | 4/2007 |
| DE | 10 2005 050 914 B4 | 4/2009 |
| DE | 10 2011 003 291 A1 | 8/2012 |
| EP | 0 092 068 A1 | 10/1983 |
| GB | 2 372 326 A | 8/2002 |
| GB | 2372326 B | 4/2005 |
| JP | 2011232295 A | 11/2011 |
| RU | 84563 U1 | 7/2009 |
| WO | 2012/100979 A1 | 8/2012 |

OTHER PUBLICATIONS

S.C. Desai et al., Hypergolic fuel detection using individual single walled carbon nanotube networks, Journal of Applied Physics, 107, Jun. 3, 2010, 114509-114509-7.
H. P. Frerichs, I. Freund, K. Hoffmann, T. Kolleth, C. Schladebach, C. Wilbertz: "Platform of Cost-Effective Gas Sensors Based on the CMOS Technology," Conference Proceedings: Sensoren im Automobilbau [Sensors in Automotive Engineering].
"H2, CO and high vacuum regeneration of ozone poisoned pseudo-Schottky Pd—InP based gas sensor" by L. Mazet, C. Varenne, A. Pauly, J. Brunet, J. P. Germain, published as "Sensors and Actuators B 103 (2004) 190-199".
Desai S et al: "Hypergolic fuel detection using individual single walled carbon nanotube networks", Journal of Applied Physics, American Institute of Physics, US, vol. 107, No. 11, Jun. 3, 2010 (Jun. 3, 2010), pp. 114509-114509.
Seals Lenward et al: "Rapid, reversible, sensitive porous silicon gas sensor", Journal of Applied Physics, American Institute of Physics, US, vol. 91, No. 4, Feb. 15, 2002 (Feb. 15, 2002), pp. 2519-2523.
Groves W A et al: "Analyzing Organic Vapors in Exhaled Breath Using a Surface Acoustic Wave Sensor Array With Preconcentration: Selection and Characterization of the Preconcentrator Adsorbent", Analytica Chimica Acta, Elsevier, Amsterdam, NL, vol. 371, Jan. 1, 1998 (Jan. 1, 1009), pp. 131-143.
English language Summary, Image 1 and Abstract from "Platform of cost-effective gas sensors based on the CMOS Technology" of Frerichs et al.

* cited by examiner

GAS-MEASURING DEVICE

CROSS REFERENCE TO RELATED APPLICATIONS

This application is a United States National Phase Application of International Application PCT/EP2015/000028 filed Jan. 9, 2015 and claims the benefit of priority under 35 U.S.C. § 119 of German Application 10 2014 000 343.4 filed Jan. 11, 2014, the entire contents of which are incorporated herein by reference.

FIELD OF THE INVENTION

The invention pertains to a sensor unit for detecting a gas, to a method for operating such a sensor unit and to a gas-measuring device with such a sensor unit.

BACKGROUND OF THE INVENTION

Gas-measuring devices are used to detect and to monitor gases and vapors in the ambient air of a human user. Gas-measuring devices are important, in particular, for detecting and monitoring toxic gases in an industrial environment and at the workplace. A very large number of toxic substances, which jeopardize the health of persons who are present, may occur in the gas phase of the ambient air in such fields of application.

Therefore, there are limit value concentrations specified by law, which must not be exceeded (maximum allowable concentrations [at the workplace], MAC from TRGS 900) for such substances. Gas-measuring devices that are portable and can be carried by the user are called personal air monitors (PAM). Strict requirements are imposed on such PAM gas-measuring devices in terms of the quantifiability of the gas measurement, reliability, safety, operability and especially the measuring time (and hence the rapidity with which a warning is generated).

The sensor or sensors, which are preferably based on chemical principles, represents/represent an important component of any gas-measuring device. Each sensor comprises at least the receptor and the transducer. The receptor interacts with analyte molecules (i.e., the gas molecules to be detected in the substance, which is, for example, a toxic substance) at the molecular level. The physicochemical property of the receptor changes in the process. This change is detected by the transducer and converted into an electrical signal.

Figure 1:
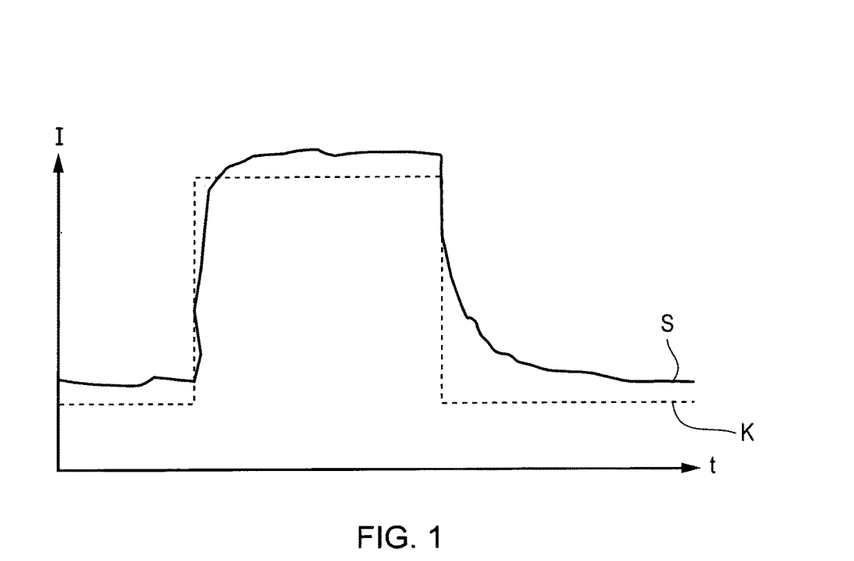
FIG. 1 is a graph illustrating the principle of a mode of operation of a prior-art chemical gas sensor.

FIG. 1 shows, for example, a gas sensor signal, which is sent when the analyte concentration in the area of the receptor assumes a rectangular course over time. The time is plotted on the x axis and the intensity I of the sensor signal S and of the analyte concentration K on the y axis. If an analyte concentration K changing in this manner over time is admitted to the receptor, the sensor usually responds with a rapid rise (response) of the transducer signal S up to a maximum, which essentially corresponds to the analyte concentration K. This change in the signal takes place during the measurement phase. The response time of a sensor is by definition (EN45544-1: 1999) 90% or 50% of the maximum signal intensity (t90, t50). The shorter the response time, the sooner can the warning about the analyte take place.

If the feed of analyte is stopped, the transducer signal usually also tends towards zero. This change in the signal takes place during the regeneration phase. The recovery time (recovery), which is defined at a drop to 10% of the signal maximum, is used in this case for the characterization.

The overall size, weight and energy consumption play an important role especially in personal air monitors. This correspondingly also applies to the gas sensors used in the gas-measuring devices.

Compact sensors with low power consumption are, for example, the capacitively-controlled field effect transistor (CCFET) gas sensors based on the mySENS technology of Micronas, Freiburg, which are also explained in the article by H. P. Frerichs, I. Freund, K. Hoffmann, T. Kolleth, C. Schladebach, C. Wilbertz: "Platform of Cost-Effective Gas Sensors Based on the CMOS Technology," Conference Proceedings: Sensoren im Automobilbau [Sensors in Automotive Engineering].

U.S. Pat. No. 3,906,473 describes a semiconductor sensor for the detection of carbon monoxide, which responds sensitively to CO at low sensor temperatures. The different reactivities of carbon monoxide and hydrocarbons at different sensor temperatures are used in U.S. Pat. No. 4,012,692 to distinguish the analytes. A semiconductor-based sensor is likewise operated at different temperatures in U.S. Pat. No. 4,185,491. Modifications are described in the documents U.S. Pat. No. 4,399,684, U.S. Pat. No. 4,567,475 and EP 0 092 068. A method for operating a breathing gas analyzer based on field effect transistor-based sensors, which provides for a measuring operation and a regeneration phase lasting up to one hour, is described in WO 2012/100979A1. DE 199 26 747 describes a receptor for detecting ammonia.

The article "$H_2$, CO and high vacuum regeneration of ozone poisoned pseudo-Schottky Pd—InP based gas sensor" by L. Mazet, C. Varenne, A. Pauly, J. Brunet, J. P. Germain, published as "Sensors and Actuators B 103 (2004) 190-199" Elsevier, described different response behaviors and desorption methods of pseudo-Schottky based gas sensors.

SUMMARY OF THE INVENTION

An object of the present invention is to provide an improved sensor unit for a gas-measuring device.

In one aspect, the present invention pertains to a sensor unit for detecting a gas, with a pressure-tight (pressure-proof) measuring channel, with a gas inlet for introducing the gas into the measuring channel, with a gas outlet for removing the gas from the measuring channel, and with a pump unit for evacuating the measuring channel, wherein the measuring channel has a gas sensor for detecting the gas and a heating unit for heating the gas sensor, and wherein the sensor unit is configured to be operated in a measuring mode and in a regeneration mode, wherein the measuring channel is evacuated and the gas sensor is heated in the regeneration mode.

The basic idea of the present invention is that an especially early and reliable gas warning can be achieved if the sensor unit of a gas-measuring device is regenerated especially thoroughly and rapidly. This is accomplished according to the present invention by the gas sensor not only being heated, but also evacuated. These two desorption processes (thermal desorption and vacuum desorption) take place essentially simultaneously. The atoms or molecules of the analyte leave the surface of the receptor solid during the desorption of the receptor of the gas sensor, so that the receptor is "cleaned" for the next measurement. The desorption is carried out according to the present invention by simultaneous heating and evacuation of the receptor especially rapidly and thoroughly in order to prepare the gas sensor for the next measuring operation. Significantly shorter response and regeneration times can thus be attained for adsorption-based sensors.

The measuring channel is configured to form a pressure-tight cavity if both the gas inlet and the gas outlet are likewise closed in a pressure-tight manner. The measuring channel may have a round, square, oblong but also bent shape. Different geometric shapes of the measuring channel make it possible to advantageously adapt the sensor unit to the spatial conditions. Thus, an especially small type of construction can be obtained, for example, with a bent measuring channel.

The gas inlet is configured to make possible the entry of gas into the measuring channel in an opened state of the gas inlet (with or without support of the pump unit) and to be closed in a pressure-tight manner in its closed state, so that the pump unit can evacuate the measuring channel. The gas inlet is preferably a valve. The valve is preferably opened and closed by a control unit.

The gas outlet is configured to make possible the outflow of gas from the measuring channel in its opened state (with or without support of the pump unit) and to be closed in a pressure-tight manner in a closed state, so that the pump unit can evacuate the measuring channel. The gas outlet preferably has a valve. The valve may be opened and closed by a control unit. The gas outlet is preferably integrated in the pump unit, i.e., the pump unit is also configured to make possible the outflow of gas from the measuring channel in a opened state (with or without support of the pumping function) and to close the measuring channel in a pressure-tight manner in the closed state.

The pump unit is configured to evacuate the measuring channel. The gas molecules detected in a current measurement process are desorbed from the receptor of the gas sensor and the receptor is prepared for the next measurement process due to the evacuation of the measuring channel and hence of the gas sensor. The pump unit may also be operated to draw gas into the measuring channel or to pump gas into same. The entry of gas into the measuring channel can thus be expedited, which in turn makes possible a more rapid measurement. The pump unit is preferably arranged at the gas outlet and is configured to evacuate the measuring channel when the gas inlet is closed. Evacuation of the measuring channel is achieved especially rapidly hereby.

The gas sensor is equipped to detect a gas, which flows past or in contact with the gas sensor. The gas sensor is preferably configured to detect the gas at a sensor or sensor surface (also called "receptor" herein) of the gas sensor. The gas sensor is preferably an adsorption-based gas sensor. A gas sensor in the sense of the present application is a functional unit that is capable of detecting a concentration of at least one chemical substance (gas or also liquid) and to convert this information into an electrical or optical signal. The gas sensor preferably converts the information on the presence of the gas to be detected in the ambient air into an electrically usable signal. The gas sensor is preferably a chemical sensor, especially an electrochemical gas sensor. The gas sensor is configured to be used reversibly in measurement processes, i.e., the gas sensor is preferably a non-consumable gas sensor.

The gas sensor preferably has a receptor and a transducer. The receptor is configured to interact with analyte molecules (i.e., the gas molecules to be detected) on a molecular level, as a result of which the physicochemical properties of the receptor undergo a change. The transducer is configured to detect these changes and to convert them into an electrical signal, which will then indicate the detection of the gas.

The heating unit is configured to heat the gas sensor, especially the receptor of the gas sensor. The gas molecules detected in a current measurement process are desorbed from the receptor due to the heating of the receptor and the receptor is thus prepared for the next measurement process. "Heating" is defined in the sense of the present application as any relative increase in temperature, be it by one or several degrees Kelvin or even hundreds of Kelvin. The reference value, from which the temperature is increased (heating), is the temperature at which the gas sensor is operated in the measuring mode. The increase against this reference temperature is carried out in the regeneration mode.

The sensor unit may be operated in a measuring mode and in a regeneration mode. The measuring channel is evacuated and the gas sensor is heated in the regeneration mode. The operation of the sensor unit is preferably controlled by a control unit. The term "control" or "controlling" also covers in the present application a "regulation" (control with feedback). The control unit may be part of the sensor unit or provided externally to this as hardware or software. When switching over from the regeneration mode to the measuring mode, the pump unit and the heating element are deactivated and the gas inlet and the gas outlet are opened. The ambient air and the analyte present in it are sent past the receptor of the gas sensor, as a result of which detection is made possible. When switching over from the measuring mode to the regeneration mode, the gas inlet and the gas outlet are closed and the pump unit and the heating element are activated. The ambient air and analyte present in the measuring channel are thus desorbed from the receptor and pumped out of the measuring channel, as a result of which the receptor is cleaned and prepared for the next detection of the gas.

In one embodiment, the gas sensor is based on a capacitively-controlled field effect transistor sensor (CCFET). An especially compact mode of construction of the sensor unit can be achieved due to the use of such a gas sensor. Further, CCFETs can be manufactured cost-effectively due to mass production; they have high sensitivity in the ppm range and long service life.

In one embodiment, the gas sensor is a cantilever sensor. A cantilever sensor has at least one so-called cantilever (or also microcantilever), which is a tiny tip, as it is also used in atomic force microscopes. The cantilever is coated with a material that specifically binds the gas molecules to be detected. Cantilevers can vibrate like a spring. If additional gas molecules are bound to the cantilever, the weight of the cantilever and thus the vibration frequency thereof, which is recorded as a measured variable, will change. If this measured variable changes, the gas is detected. Cantilever sensors have an especially high sensitivity in the ppm range.

In one embodiment, the gas sensor is a Surface-Acoustic Wave Sensor (SAW). Surface waves propagate in a SAW gas sensor on a piezo crystal and are converted into voltage fluctuations. If the analyte is bound to a material arranged on the piezo crystal, the weight of the piezo crystal and hence the wave characteristic (travel time or velocity of propagation, amplitude, frequency) of the surface wave will change on the piezo crystal. This change is reflected in the voltage fluctuations, as a result of which the analyte is detected. The SAW gas sensors advantageously also have a rapid response characteristic and long service life.

The above-mentioned gas sensors have advantages in the sense that they are very compact, which makes, in turn, possible a more compact mode of construction of the sensor unit and hence of the gas-measuring device. Further, their energy consumption is low, so that the sensor unit can be operated over a longer period of time. Their response times for the measurement process and the temperature control, i.e., the heating as well as the subsequent cooling, are also relatively short, so that rapid measurement and preparation for the next measurement are made possible. This is essential for guaranteeing early warning about a gas that is present.

In one embodiment, the sensor unit is operated for a shorter time in the measuring mode than in the regeneration mode. The duration of the measuring mode is consequently shorter than the duration of a regeneration mode. The sensor unit is preferably operated in the measuring mode for less than a minute, preferably for less than 10 seconds, and especially preferably for less than one second. The sensor unit is preferably operated in the regeneration mode for less than 10 minutes, preferably for less than one minute, and especially preferably for less than 10 seconds. The sensor unit is preferably operated alternatingly in the measuring mode and in the regeneration mode. One cycle of measuring mode and regeneration mode preferably lasts less than 5 minutes and especially preferably less than one minute. The shorter one cycle of measuring mode and regeneration mode, the sooner can a warning be issued before a limit value of the gas to be detected is exceeded.

In one embodiment, the heating unit is configured to heat the gas sensor to 20° C. to 400° C. and preferably to 30° C. to 150° C. As was already explained above, lower and higher temperatures are, however, also possible; the only thing that is essential being that the gas sensor be heated in the regeneration mode rather than in the measuring mode. The heating element is configured, in particular, to heat the sensor surface or the receptor of the gas sensor.

In one embodiment, the pump unit is configured to generate a vacuum of less than 500 mbar, preferably less than 100 mbar and especially preferably less than 5 mbar in the measuring channel. The pump unit is configured, in particular, to generate a vacuum of less than 500 mbar, preferably less than 100 mbar and especially preferably less than 5 mbar at the sensor or the receptor of the gas sensor. The vacuums mentioned are absolute pressures, so that the particular pressure mentioned prevails in the measuring channel or at least in the area of the receptor.

In one embodiment, the sensor unit has, further, a computer for determining a gas concentration. The computer is, for example, a computing unit. The determination of the gas concentration comprises a calculation or other derivation of the gas concentration from measured variables, such as the measuring time, signal change, temperature pressure, etc. The computer is preferably configured to determine the concentration of the gas on the basis of the change in the signal over the measuring time. The computer especially preferably determines the gas concentration on the basis of the slope of the change in the signal over the measuring time.

In another aspect, the present invention pertains to a gas-measuring device with a sensor unit according to the present invention. A preferred gas-measuring device for use with a sensor unit according to the present invention is described in DE 10 2005 050 914 A1 and B4, to the specifications and teachings of which reference is made here. The gas-measuring device is preferably a portable device. In particular, the gas-measuring device is a PAM device.

In another aspect, the present invention pertains to a method for operating a sensor unit according to the present invention, wherein the method has a measuring mode and a regeneration mode and wherein the regeneration mode comprises the evacuation of the measuring channel and the heating of the gas sensor.

The above-described embodiments may be combined with one another and with the above-described aspects as desired in order to achieve advantages according to the present invention. Preferred combinations of above-described embodiments will be described below as examples. The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 2:
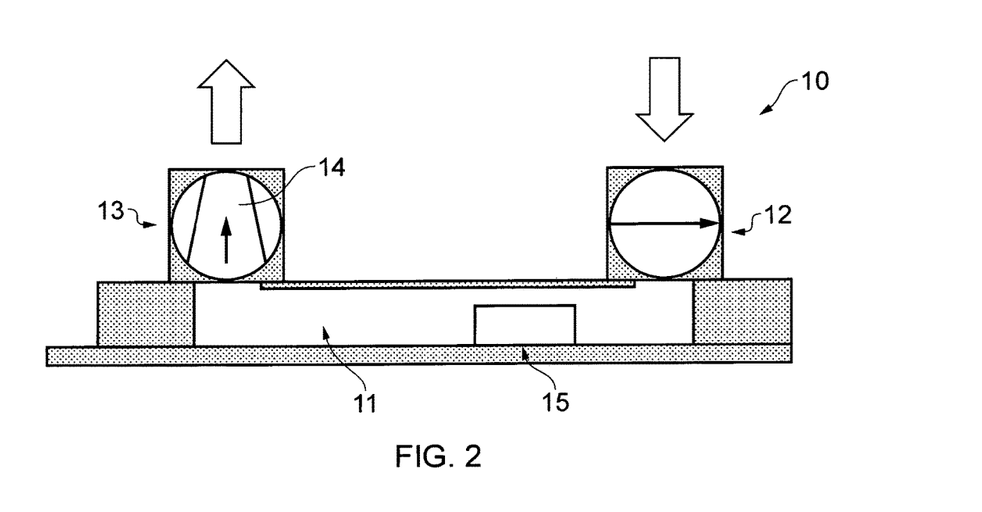
FIG. 2 is a schematic sectional view showing an exemplary embodiment of a sensor unit according to the present invention.

Referring to the drawings, FIG. 2 shows a schematic view of the configuration of a sensor unit 10. The sensor unit 10 is configured for the detection of a gas and has: A pressure-tight measuring channel 11, a gas inlet 12 for introducing (indicated by an arrow) the gas into the measuring channel 11, a gas outlet 13 for removing (likewise indicated by an arrow) the gas from the measuring channel 11, and a pump unit 14 for evacuating the measuring channel 11.

The measuring channel 11 has a gas sensor 15 for detecting the gas and a heating unit 16 for heating the gas sensor 15. The sensor unit 10 is configured to be operated in a measuring mode and a regeneration mode. The measuring channel 11 is evacuated and the gas sensor 15 is heated in the regeneration mode, as a result of which rapid and thorough desorption is achieved.

Figure 3:
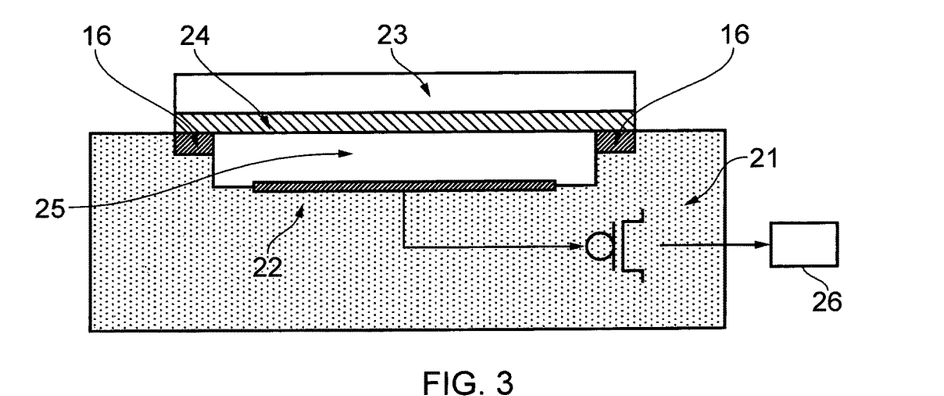
FIG. 3 is a schematic sectional view of an exemplary embodiment of a CCFET gas sensor according to the present invention.

The gas sensor is, for example, a CCFET (as is shown in FIG. 3), which is integrated in the pressure-tight channel 11. This measuring channel 11 may be closed on its two sides: With a shut-off valve 12 on the side on which the gas is fed and by a pump 14, which at the same time forms the gas outlet 13, on the side on which the gas is removed.

FIG. 3 shows a CCFET gas sensor. Integrated in a semiconductor component, a field-effect transistor 21 is in connection with electrodes 22 and 23, which are, in turn, capacitively coupled with a gas-sensitive layer (receptor) 24. The gas-sensitive layer 24 interacts, depending on the analyte concentration, with the gas molecules in the air gap 25. The adsorbed analyte molecules change the surface potential of the gas-sensitive layer 24. This change leads to a change in the potential between the electrodes 22 and 23 and is detected by FET 21 and is transmitted to the transducer 26. A heating unit 16 is provided for heating the gas-sensitive layer 24.

Figure 4:
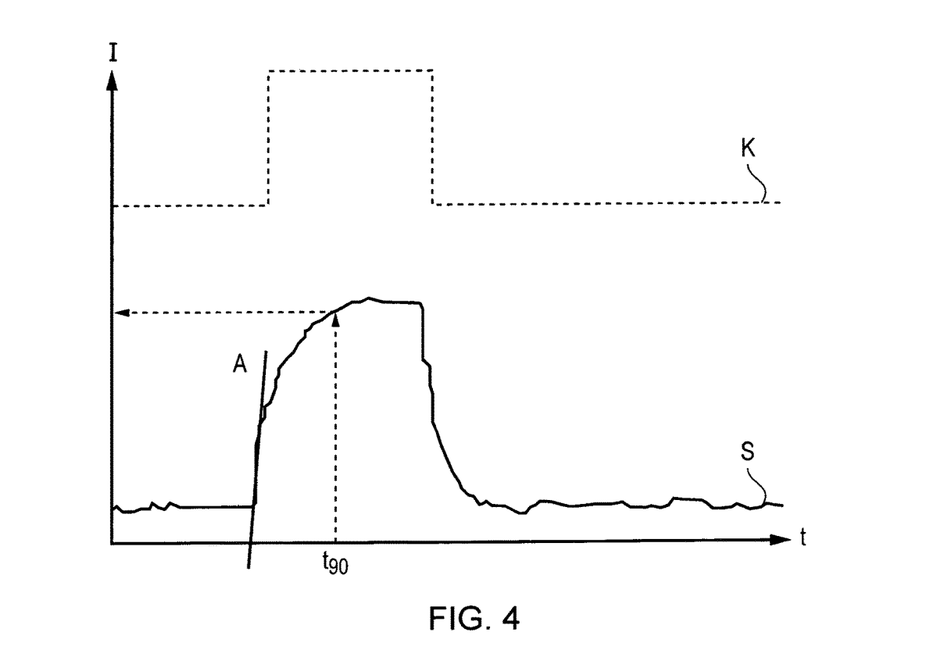
FIG. 4 is a graph illustrating a process for detecting the analyte by a prior-art chemical gas sensor.

A time-dependent signal S, as is shown in FIG. 4, is practically obtained with the use of CCFETs known in the state of the art. The sensor operation is divided into two time ranges: A measurement phase and a regeneration phase. The signal obtained for a rectangular course of the analyte concentration K shows a nearly linear rise at the beginning, the slope A becoming increasingly smaller with increasing load to eventually become zero. The duration of the latter is, as a rule, several hours.

This leads to relatively long response times if the characterization according to t90 is used as the basis. Very long regeneration times (t10) are correspondingly also found in practice. Both are unacceptable for gas detectors.

To shorten the regeneration time, a gas sensor 15 according to the present invention is thermally heated at times and evacuated essentially at the same time. This leads to a substantially more rapid desorption.

FIG. 4 shows a detection operation for an analyte with the determination of the slope A of the sensor signal S as an indicator of the analyte concentration K. The sample air to be analyzed is moved past the gas sensor 15 or the receptor 24 thereof through the measuring channel 11 by means of the pump unit 14. The pressure nearly corresponds to the corresponding ambient pressure. The analyte molecules are bound to the surface of the receptor 24 on suitable receptor structures, especially on receptor molecules. The binding, once having taken place, leads to a change in the surface properties of the receptor 24, which can, in turn, be detected in the form of a change in the voltage. A signal, whose course over time is shown in FIG. 4, is generated on the basis of the change in the surface property, especially on the basis of the change in the voltage. The slope A of the signal, which is likewise detected, is of particular interest.

What is especially of interest for the analysis is the part of the signal curve S, which is generated at a time at which the number of places of the receptor 24, which have already absorbed analyte, is still significantly lower than the total number of available adsorption spaces. The slope A is determined within this rather short time period (for example, less than 15 sec). The gas inlet of the measuring channel 11 is then closed and the measuring channel 11 is evacuated with the pump unit 14. At the same time, the gas sensor 15 or its receptor 15 is heated by means of the heating unit 16. More rapid removal of both the desorbed analyte molecules and the analyte molecules present in the gas phase, which have not yet been bound to the receptor surface during the measurement, is achieved due to this combination of a thermal desorption as well as vacuum desorption. This procedure is markedly more effective than a simple desorption based only on an increase in temperature or evacuation, as it can be determined from FIGS. 5a through 5c.

Figure 5A:
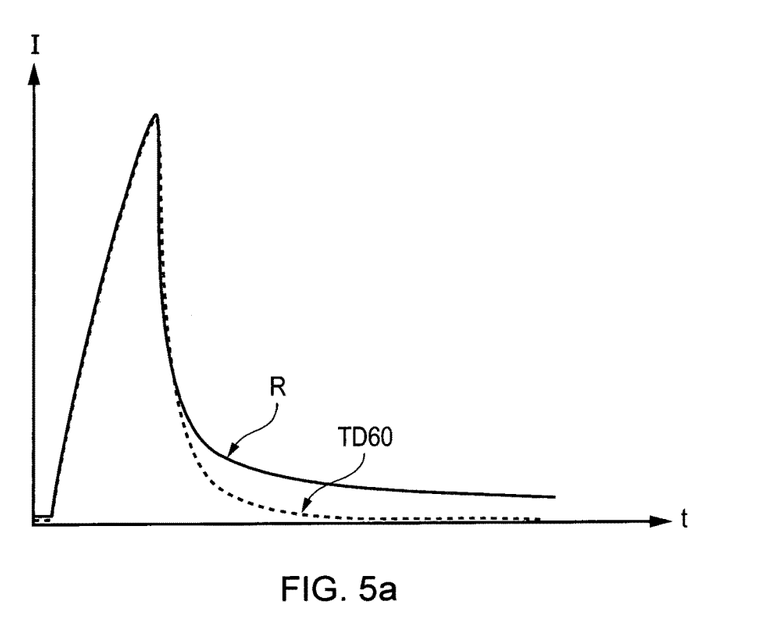
FIG. 5a is a graph of sensor signals during measurement phases and regeneration phases.
Figure 5B:
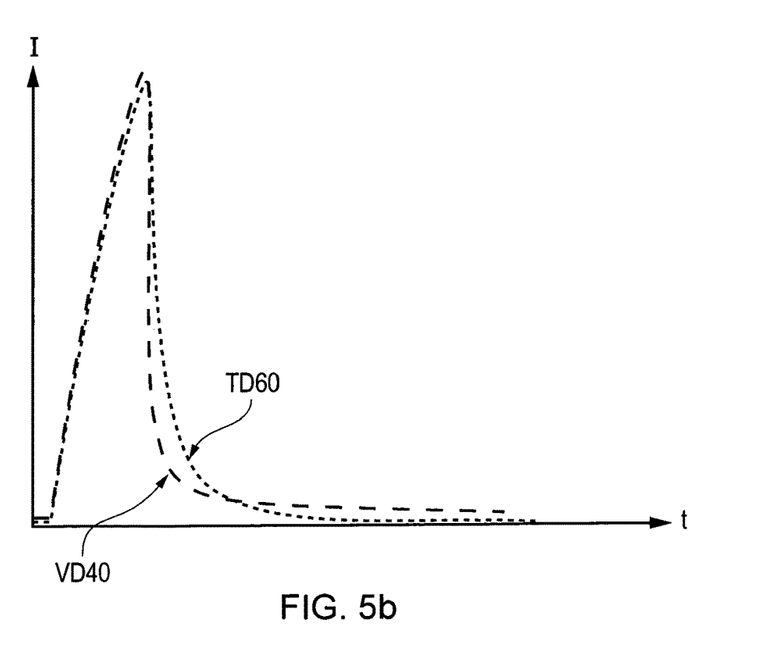
FIG. 5b is a graph of sensor signals during measurement phases and regeneration phases.
Figure 5C:
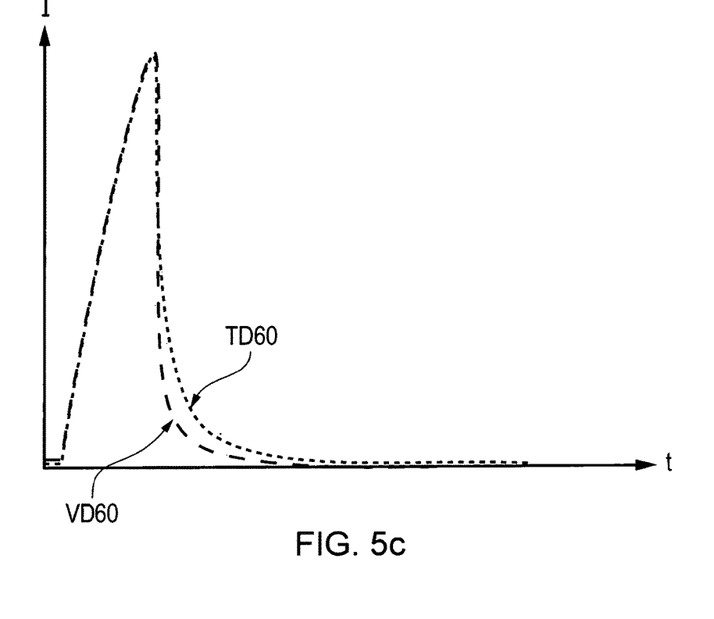
FIG. 5c is a graph of sensor signals during measurement phases and regeneration phases.

FIGS. 5a through 5c are signal curves S during the measurement phases and the regeneration phases.

FIG. 5a shows a comparison of the sensor signals S at a gas sensor temperature (or the temperature on the receptor surface) of 40° C. and at an increased gas sensor temperature of 60° C. for thermal desorption.

In FIG. 5a through 5c, the solid line R describes the curve for a receptor surface temperature of 40° C. Curve R rises at first nearly linearly. The feed of analyte is then interrupted, and the signal R drops markedly, without reaching the zero value during the time period being considered. Consequently, there remains a rest of adsorbed analyte molecules. The broken line TD60 describes the curve obtained when the gas sensor 15 is heated to 60° C. after interruption of the analyte feed. This causes the curve to tend towards the zero value more rapidly.

FIG. 5b shows a comparison of the sensor signals S at an increased gas sensor temperature of 60° C. for thermal desorption and for vacuum desorption at 40° C.

FIG. 5b likewise shows the curve TD60 for the thermal desorption at 60° C. It is compared with the curve VD40 obtained if the measuring channel 11 with the gas sensor 15 is evacuated. The signal VD40 drops markedly more rapidly than the signal TD60 during the thermal desorption, but then it crosses the curve TD60 of thermal desorption and does not reach the zero value during the time period being considered.

The sensor signals S, which are generated at an elevated gas sensor temperature of 60° C. for thermal desorption, and the sensor signals S, which can be seen at an elevated gas sensor temperature during a combination of vacuum desorption and thermal desorption at 60° C., are compared with one another in FIG. 5c.

The curve TD60 of thermal desorption at 60° C. is compared in FIG. 5c with the curve VD60 of vacuum desorption at 60° C. The signal VD6-0 drops markedly more steeply than the signal TD60 and it also reaches the zero value, which corresponds to an essentially complete desorption of the analyte molecules from the receptor surface, relatively early. If the zero value is reached, the next measurement can be performed after opening the shut-off valve at the gas inlet 12.

Figure 6:
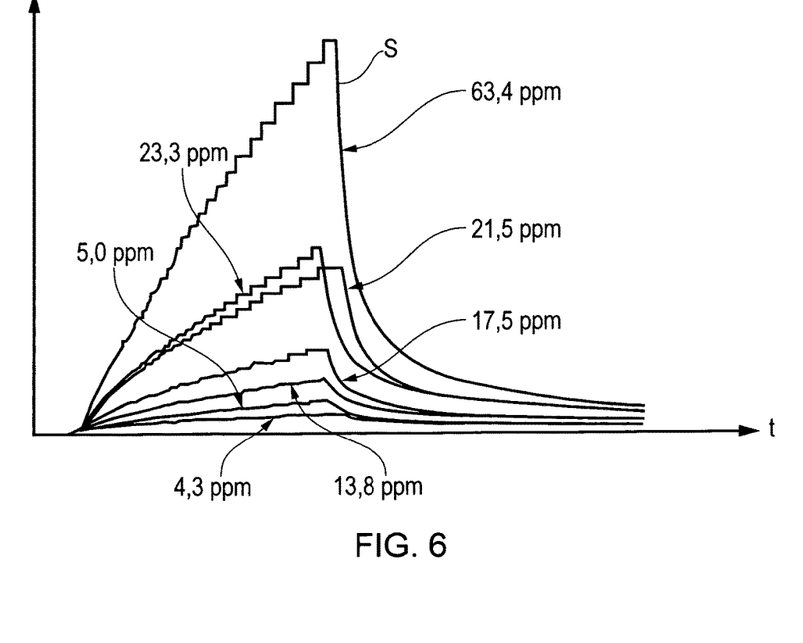
FIG. 6 is a graph of sensor signals for different analyte concentrations.
Figure 7:
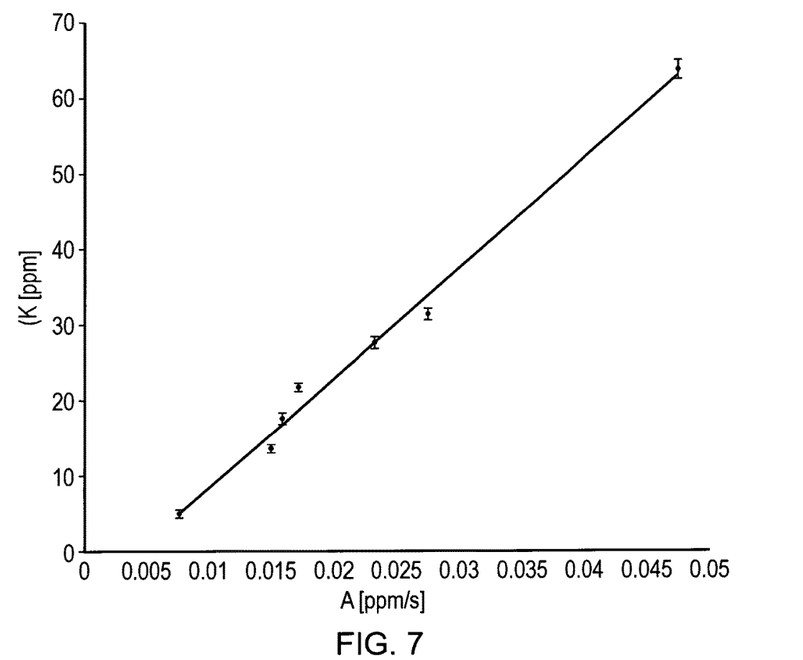
FIG. 7 is a graph of the relationship between the slope of the sensor signals in FIG. 6 and the analyte concentrations.

FIG. 6 shows different sensor signals S at different analyte concentrations K. The time-dependent sensor signal curves S differ at different analyte concentrations K, which is illustrated in FIG. 7. Different ammonia concentrations were admitted to a CCFET from Micronas for the comparison measurements shown in FIG. 6. The change in the signal in mV is detected during a measurement phase (for example, over 10 sec) and the corresponding slope A is determined. The signal changes depend on the analyte concentration K. The higher the analyte concentration K., the greater is the corresponding slope A.

FIG. 7 shows the relationship between the slope A of the sensor signals S in FIG. 6 and the analyte concentrations K. The slopes A determined after 10 sec are plotted in FIG. 7 against the corresponding analyte concentrations K. There is a linearity between the slope A of the sensor signal and the analyte concentration K, which can be used by the computer 17 to determine the gas concentration if the slope A of the sensor signal is available as a measured value.

The measurement phase is followed by the regeneration phase. The regeneration phase is, as a rule, longer in time than the measurement phase, e.g., 50 sec. The feed of the sample gas is interrupted, the shut-off valve is closed and the gas phase present above the receptor 24 is drawn off with the pump 14. This is shown in FIGS. 5 and 6, in which the signal intensity I drops to zero during the regeneration phase, because the analyte molecules, which have been bound to the receptor 24 during the measurement phase, are desorbed nearly completely during the subsequent regeneration phase.

Figure 8:
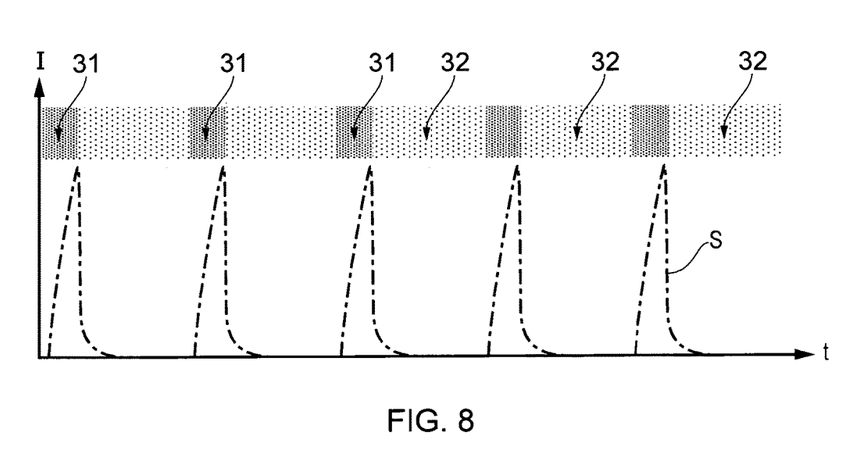
FIG. 8 is a graph of a time diagram for the measurement and regeneration modes.

FIG. 8 is a time diagram for the measurement and regeneration phases 31, 32. FIG. 8 shows recurring intervals (cycles) comprising a measurement phase 31 and a regeneration phase 32 with the corresponding sensor signal curve S at constant analyte concentration K. The measurement of the analyte is carried out, for example, at one-minute intervals.

A regeneration mode according to the present invention offers above all the following advantages: The early determination of the analyte concentration K from the slope A compared to a known t90 determination (see FIG. 4) is advantageous especially for gas-measuring devices 100 in which the rapidity of the measurement and warning is directly relevant for the safety and health of the user. The combination of vacuum desorption and thermal desorption leads to an especially effective cleaning and desorption of the receptor surface. Thorough desorption is, in turn, a prerequisite for the use of the slope method described. The receptor surface is generally contaminated with few analyte molecules. This also increases the service life of the receptor.

Figure 9:
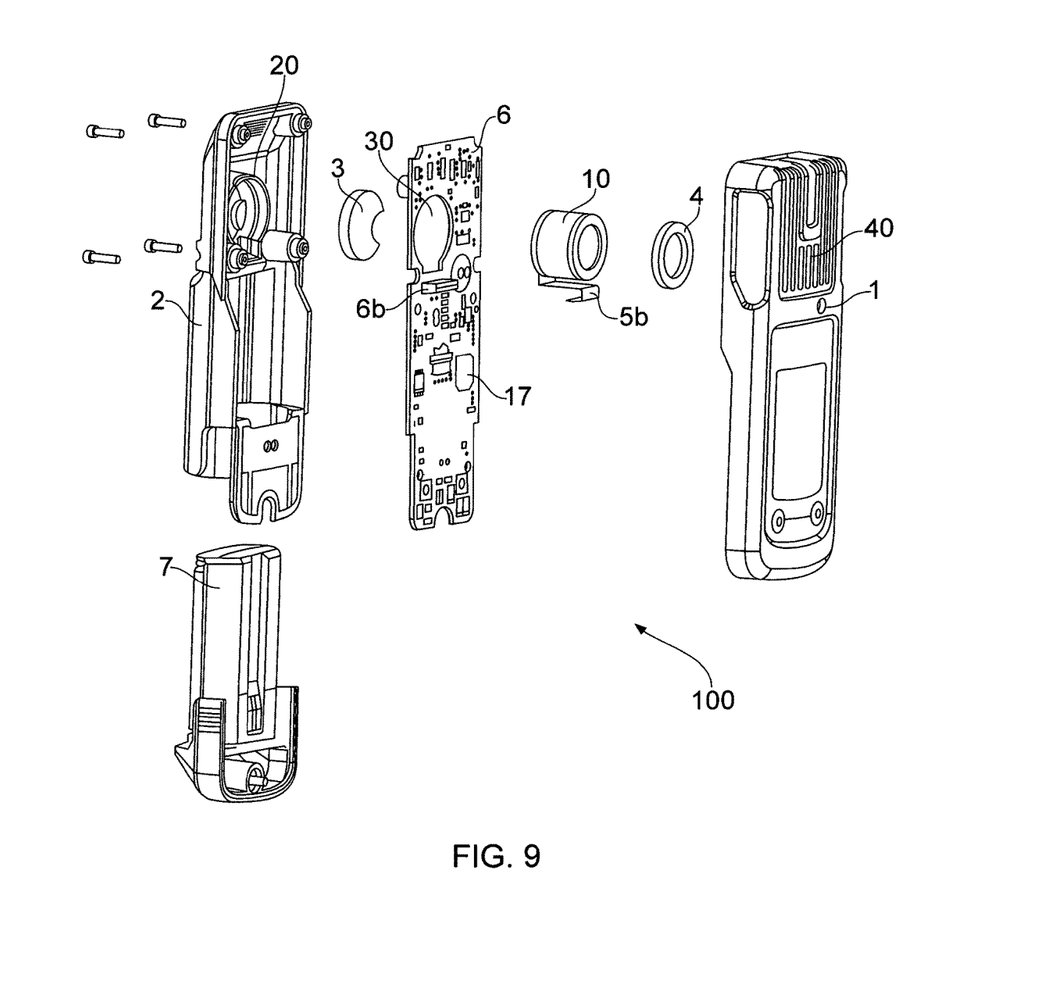
FIG. 9 is an exploded view of an exemplary embodiment of a gas-measuring device according to the present invention.

The portable gas-measuring device 100 according to FIG. 9 has a housing, which is composed of a plurality of housing parts, especially a front shell 1 and a rear shell 2. A ring-shaped holding element 20 is provided on the two inner sides of the housing for receiving the sensor unit 10. Damping intermediate elements 3, 4, made, for example, from a foamed polymer or from a cellular rubber, are arranged in front of and behind the sensor unit 10. Further, the printed circuit board 6 has an opening 30 for receiving the sensor unit 10. In addition, the computer 17 is provided on the printed circuit board 6, but the computer unit 17 and the control unit may also be integrated in the sensor unit 10.

The sensor unit 10 is connected to the plug 6b via a flexible connection element 5b.

The openings 40 in the housing establish a gas flow connection to the surrounding area. The component is an optional housing part, which is used as an electrical supply unit 7 (for example, battery).

A plurality of electrochemical gas sensors 10 are additionally provided for a multiple gas-measuring device 100 for the specific measurement of certain gases, especially $O_2$, $Cl_2$, CO, $CO_2$, $H_2$, $H_2S$, HCN, $NH_3$, NO, $NO_2$, $PH_3$, $SO_2$, amines, odorant, $COCl_2$ and organic vapors.

The gas-measuring device 100 is preferably configured for use in an explosion-protected area by corresponding tightness of the composite housing and/or by an explosion-tight configuration of the electrical components.

Figure 10:
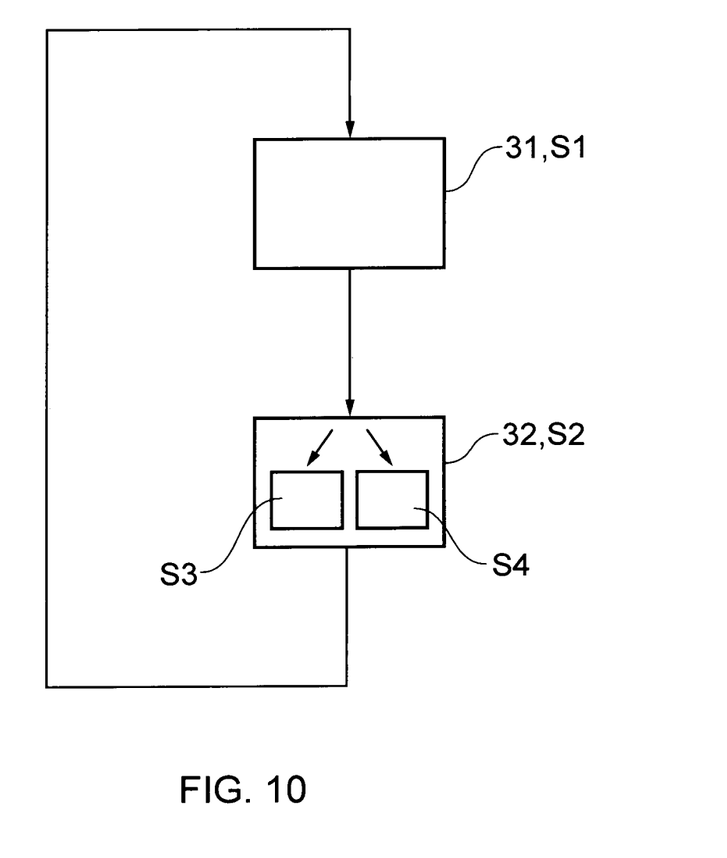
FIG. 10 is a schematic view of an exemplary embodiment of a method for operating a sensor unit according to the present invention.
Figure 11:
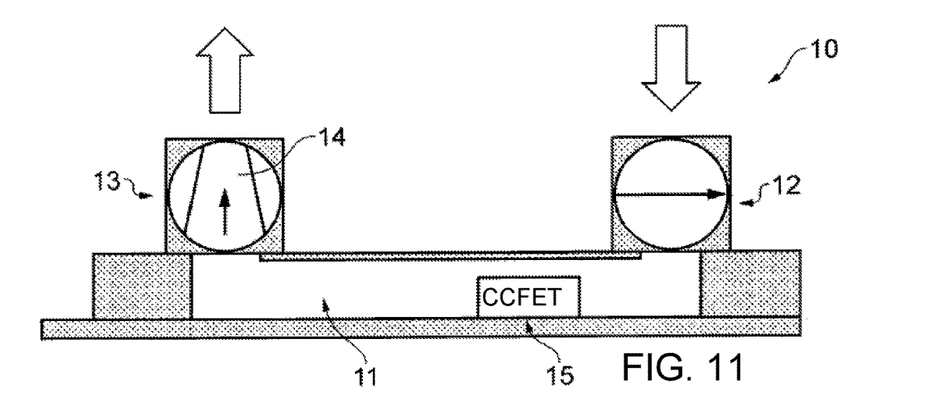
FIG. 11 is a schematic sectional view showing the exemplary embodiment of a sensor unit of FIG. 2 with a CCFET sensor as the sensor.
Figure 12:
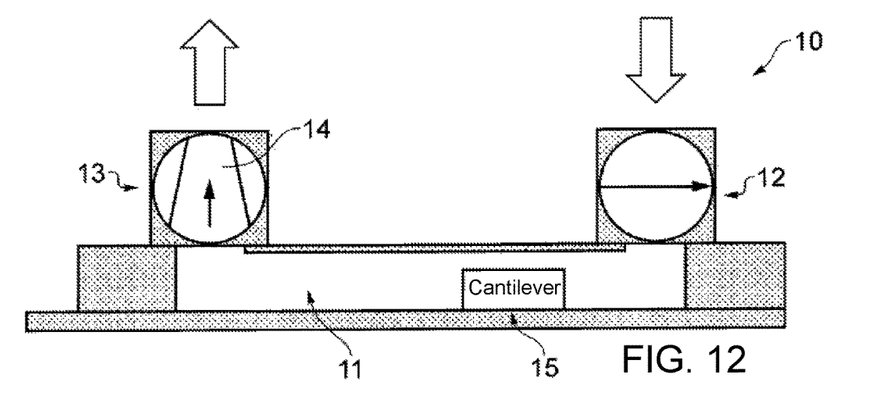
FIG. 12 is a schematic sectional view showing the exemplary embodiment of a sensor unit of FIG. 2 with a cantilever sensor (cantilever) as the sensor.
Figure 13:
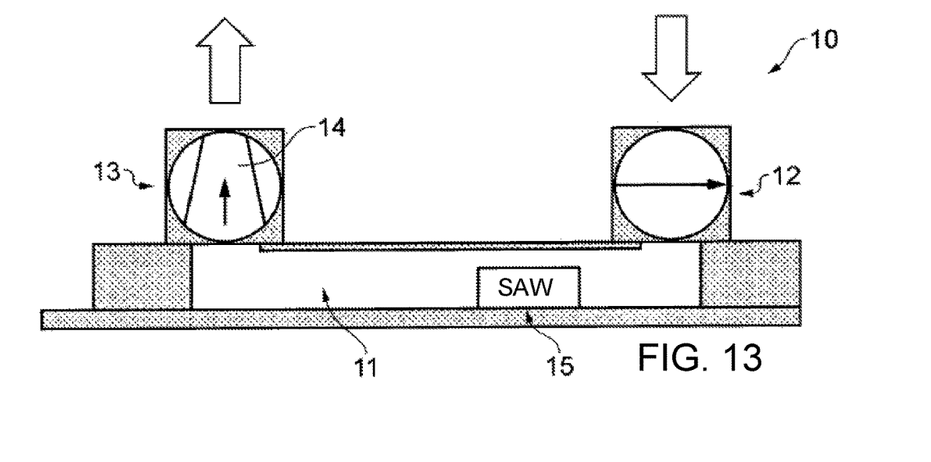
FIG. 13 is a schematic sectional view showing the exemplary embodiment of a sensor unit of FIG. 2 with a Surface-Acoustic Wave Sensor (SAW) as the sensor.

FIG. 10 shows a sequence of measurement and regeneration phases. In a first step S1, the sensor unit 10 is operated in a measuring mode and the measurement phase 31 is carried out in order to make it possible to detect an analyte.

In a second step S2, the sensor unit 10 is operated in the regeneration mode and the regeneration phase 32 is carried out. The regeneration phase 32 comprises a step S3 of evacuating the measuring channel 11 and the receptor 24 and a step S4 of heating the gas sensor 15 and the receptor 24.

After conclusion of the regeneration phase 32, the receptor 24 is prepared for a new measurement and the next cycle of the method begins with the performance of the next measuring mode 31.

While specific embodiments of the invention have been shown and described in detail to illustrate the application of the principles of the invention, it will be understood that the invention may be embodied otherwise without departing from such principles.

The invention claimed is:

1. A sensor unit for detecting a gas, the sensor unit comprising:
    a measuring channel;
    a gas inlet for introducing environmental gas into the measuring channel;
    a gas outlet for removing the environmental gas from the measuring channel;
    a shut off valve operatively connected to one of the gas inlet and the gas outlet and configured to close the measuring channel at said one of the gas inlet and the gas outlet;
    a pump unit operatively connected to another of the gas inlet and the gas outlet and configured to evacuate environmental gas from the measuring channel by generating a vacuum therein and to close the measuring channel at said other of the gas inlet and the gas outlet, whereby with the shut off valve and the pump unit closing the gas inlet and the gas outlet, the measuring channel is pressure-tight with respect to environmental gas;
    a gas sensor operatively connected to the measuring channel for detecting the gas in the environmental gas; and
    a heating unit for heating the gas sensor, wherein the sensor unit is configured to be operated in a measuring mode and in a regeneration mode, wherein the measuring channel is evacuated and the gas sensor is heated in the regeneration mode; and
    a control unit controlling an operation state of each of the shut off valve, the pump unit and the heating unit and switching over from the regeneration mode to the measuring mode including deactivating the pump unit and the heating element and opening the gas inlet and the gas outlet and switching over from the measuring mode to the regeneration mode including closing the gas inlet and the gas outlet and activating the pump unit and the heating element.

2. The sensor unit in accordance with claim 1, wherein the gas sensor is a capacitively controlled field-effect transistor sensor (CCFET).

3. The sensor unit in accordance with claim 1, wherein the gas sensor is a cantilever sensor.

4. The sensor unit in accordance with claim 1, wherein the gas sensor is a surface-acoustic wave sensor (SAW).

5. The sensor unit in accordance with claim 1, wherein the sensor unit is operated for a shorter time in the measuring mode than in the regeneration mode.

6. The sensor unit in accordance with claim 1, wherein the heating unit is configured to heat the gas sensor to 20° C. to 400° C.

7. The sensor unit in accordance with claim 1, wherein the pump unit is configured to generate a vacuum of less than 500 mbar.

8. The sensor unit in accordance with claim 1, further comprising a computer configured to determine a gas concentration based on a change in a sensor signal with respect to a time period during the measuring mode.

9. A personal air monitoring gas-measuring device comprising:
a housing defining a housing interior and having an opening in the housing to establish a gas flow connection to environmental gas of a surrounding area;
a sensor unit disposed in the housing adjacent to the opening with a gas flow connection to the environmental gas of the surrounding area, the sensor unit comprising:
a measuring channel;
a gas inlet for introducing the environmental gas into the measuring channel;
a gas outlet for removing the environmental gas from the measuring channel;
a shut off valve operatively connected to one of the gas inlet and the gas outlet and configured to close the measuring channel at said one of the gas inlet and the gas outlet;
a pump unit operatively connected to another of the gas inlet and the gas outlet and configured to move the environmental gas from the gas inlet to the gas outlet through the measuring channel and to evacuate environmental gas from the measuring channel by generating a vacuum therein with the shut off valve closing the measuring channel at said one of the gas inlet and the gas outlet and to close the measuring channel at said other of the gas inlet and the gas outlet, whereby with the shut off valve and the pump unit closing the gas inlet and the gas outlet, the measuring channel is pressure-tight with respect to environmental gas;
a gas sensor operatively connected to the measuring channel for detecting a gas in the environmental gas; and
a heating unit for heating the gas sensor, wherein the sensor unit is configured to be operated in a measuring mode and in a regeneration mode, wherein the measuring channel is evacuated and the gas sensor is heated in the regeneration mode; and
a control unit that is a part of the sensor unit or is disposed in the housing and connected to the sensor unit, the control unit controlling an operation state of each of the shut off valve, the pump unit and the heating unit and switching over from the regeneration mode to the measuring mode including deactivating the pump unit and the heating element and opening the gas inlet and the gas outlet and switching over from the measuring mode to the regeneration mode including closing the gas inlet and the gas outlet and activating the pump unit and the heating element.

10. The personal air monitoring gas-measuring device in accordance with claim 9, further comprising a computer that is a part of the sensor unit or is disposed in the housing and is connected to the sensor unit, wherein the computer is configured to determine a gas concentration based on a change in a sensor signal with respect to a time period during the measuring mode.

11. The personal air monitoring gas-measuring device in accordance with claim 10, further comprising an electrical supply unit disposed in the housing and is connected to the pump unit, connected to the gas sensor, connected to the heating unit, connected to the control unit and connected to the computer for mobile operation of the personal air monitoring gas-measuring device as a personal air monitor.

12. A method comprising the steps of:
providing a sensor unit comprising a measuring channel, a gas inlet for introducing environmental gas into the measuring channel, a gas outlet for removing the environmental gas from the measuring channel, a shut off valve operatively connected to one of the gas inlet and the gas outlet and configured to close the measuring channel at said one of the gas inlet and the gas outlet, a pump unit operatively connected to another of the gas inlet and the gas outlet and configured to evacuate the environmental gas from the measuring channel by generating a vacuum therein via said other of the gas inlet and the gas outlet, whereby with the shut off valve and the pump unit closing the gas inlet and the gas outlet, the measuring channel is pressure-tight with respect to environmental gas, a gas sensor operatively connected to the measuring channel for detecting a gas in the environmental gas and a heating unit for heating the gas sensor, and a control unit that is part of the sensor unit or is connected to the sensor unit, the control unit controlling an operation state of each of the shut off valve, the pump unit and the heating unit;
operating the sensor unit in a measuring mode; and
operating the sensor unit in a regeneration mode comprising:
closing the gas inlet and the gas outlet to the environmental gas and evacuating the measuring channel with the pump controlled by the control unit; and
heating of the gas sensor; and
switching over from the regeneration mode to the measuring mode at recurring intervals to cycle between the measurement mode and the regeneration mode.

13. The method in accordance with claim 12, wherein the gas sensor is a capacitively controlled field-effect transistor sensor (CCFET).

14. The method in accordance with claim 12, wherein the gas sensor is a cantilever sensor.

15. The method in accordance with claim 12, wherein the gas sensor is a surface-acoustic wave sensor (SAW).

16. The method in accordance with claim 12, wherein the sensor unit is operated for a shorter time in the measuring mode than in the regeneration mode.

17. The method in accordance with claim 12, wherein the heating unit is configured to heat the gas sensor to 20° C. to 400° C.

18. The method in accordance with claim 12, wherein the pump unit is configured to generate a vacuum of less than 500 mbar.

19. The method in accordance with claim 12, wherein the sensor unit further comprises a computer configured to determine a gas concentration based on a change in a sensor signal with respect to a time period during the measuring mode.

20. The method according to claim 19, further comprising:
providing the sensor unit in a housing; and
providing an electrical supply unit disposed in the housing and connected to the pump unit, connected to the gas sensor, connected to the heating unit, connected to the control unit and connected to the computer for mobile operation of the sensor unit in the housing to provide a personal air monitor.

* * * * *